| United States Patent [19] | [11] | 4,218,475 |
|---|---|---|
| Wagner et al. | [45] | Aug. 19, 1980 |

[54] HYPOLIPIDEMIC BENZYLAMINOBENZENE ALKANOIC OR ALKENOIC ACIDS

[75] Inventors: Eugene R. Wagner, Carmel; Donald P. Matthews, Indianapolis; Alfred A. Renzi, Zionsville, all of Ind.

[73] Assignee: The Dow Chemical Company, Midland, Mich.

[21] Appl. No.: 955,041

[22] Filed: Oct. 26, 1978

[51] Int. Cl.$^2$ .............................................. A01N 9/20
[52] U.S. Cl. .................................. 424/319; 424/309; 424/282; 560/45; 560/47; 560/48; 562/452; 562/456; 562/457; 260/340.5 R
[58] Field of Search ................... 260/340.5 R; 560/45, 560/47, 48; 562/457, 456, 452; 424/309, 319, 282

[56] References Cited

U.S. PATENT DOCUMENTS

| 3,673,243 | 7/1972 | Yamamoto et al. | 562/457 |
|---|---|---|---|
| 3,766,260 | 10/1973 | Carney et al. | 562/457 |
| 3,839,433 | 10/1974 | Wasley | 562/457 |
| 3,919,304 | 11/1975 | Rossi | 562/457 |
| 3,957,850 | 5/1976 | Bouchara | 562/457 |
| 4,026,896 | 5/1977 | Harita et al. | 562/456 |

OTHER PUBLICATIONS

Derwent Abst., Be-863-156, (7-20-1978).

*Primary Examiner*—Norman Morgenstern
*Assistant Examiner*—James H. Reamer

[57] ABSTRACT

Substituted or unsubstituted benzylaminobenzene alkanoic or alkenoic acids are disclosed as hypolipidemic agents and especially as hypocholesterolemic agents; along with a method of use and pharmaceutical compositions thereof.

7 Claims, No Drawings

HYPOLIPIDEMIC BENZYLAMINOBENZENE ALKANOIC OR ALKENOIC ACIDS

BACKGROUND OF THE INVENTION

As established by various studies, it is recognized that cholesterol and triglycerides play a major role in the formation of atherosclerotic plaques by accelerating the deposition of blood lipids in the arterial walls. Hypercholesterolemia, i.e. elevated cholesterol levels of the blood, has been the cause of special concern, and agents having hypocholesterolemic activity are used in the treatment of atherosclerosis. See U.S. Pat. No. 3,262,850.

Various benzylaminobenzoic acid derivatives have been described as having hypolipidemic activity, i.e. hypocholesterolemic and hypotriglyceridemic activity. See Dutch publication No. 7,602,332. Surprisingly the adjacent homologues of the known hypolipidemic compounds, i.e. benzylamino benzeneethanoic acids, although active as hypotriglyceridemic agents are not effective in lowering the cholesterol levels in the blood. For this reason it is particularly surprising that the class of compounds described herein are active hypocholesterolemic agents.

SUMMARY OF THE INVENTION

The present invention relates to novel substituted or unsubstituted benzylaminobenzene alkanoic or alkenoic acids, their use in lowering elevated serum lipid levels, especially serum cholesterol levels, in a mammal and the pharmaceutical compositions thereof. Compounds falling within the scope of the present invention may be represented by the general formula

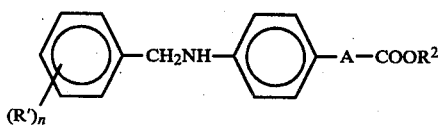

wherein R' independently and at each occurrence represents halogen, lower alkyl, lower alkoxy, or methylenedioxol; $R^2$ is hydrogen or lower alkyl; n is the integer 0, 1, 2 or 3; and A is ethylidene or a saturated hydrocarbon of the general formula $-(CH_2)_m-$ wherein m is an integer of from 2 to about 3 with the proviso that when m is 3, R' is not methylenedioxol. As used in the specification and claims the term lower alkyl and lower alkoxy refers to a moiety having from 1 to about 3 carbon atoms. The term halogen refers to a halogen substitution selected from the group consisting of chloro, fluoro, or bromo with chloro and fluoro substitutions being preferred.

Pharmaceutically-acceptable salts of the benzylaminobenzene alkanoic or alkenoic acids are considered as being within the scope of this invention. Pharmaceutically-acceptable salts refer to the acid addition salts of those bases which will form a salt with the carboxylic acid and which will not cause an adverse physiological effect when administered to an animal at dosages consistent with good pharmacological activity. Suitable bases thus include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like, ammonia, primary, secondary, and tertiary amines and the like. Also aluminum salts of the instant compounds may be obtained by treating the corresponding sodium salt with an appropriate aluminum complex such as, for example, aluminum chloride hexahydrate, and the like.

The benzylaminobenzene alkanoic acids described above, their esters and pharmaceutically-acceptable salts when used according to the method of the present invention show hypocholesterolemic activity, i.e. lower the cholesterol levels in the serum, in mammals. The compounds disclosed herein are therefore useful in the treatment of hypercholesterolemia in mammals. The compounds used in the practice of the present invention are also suitable for use in the treatment of hyperilipidemia in mammals characterized by elevated cholesterol and triglyceride levels in the blood. The compounds can be administered internally to the mammal either orally or parenterally by subcutaneous, intravenous, or intraperitonel injection or by implantation or the like. Oral administration is generally preferred.

The effective hypolipidemic amount of the active compound to be internally administered to a mammal, that is the amount which is effective to significantly lower the amount of cholesterol and triglycerides in the blood, can vary depending upon such factors as the particular benzylaminobenzene alkanoic acid compound, ester or pharmaceutically-acceptable salt employed, the desired lipid level to be obtained, the severity of the disease, the period of administration, and the route of administration. In general, an effective daily dosage range is from about 25 to about 400 milligrams per kilogram of body weight, with a daily dosage range of from about 25 to about 50 milligrams per kilogram of body weight being preferred. The effective hypocholesterolemic amount of the active compound, i.e. the amount which is effective to significantly lower the amount of cholesterol in the blood, generally falls within the same dosage range as the hypolipidemic amount and although not the same as the effective hypolipidemic amount is subject to the same general variables. Therefore, the proper dosage may be readily determined by one skilled in the art from the general method described herein.

DETAILED DESCRIPTION OF THE INVENTION

The active compounds described herein are prepared by condensing a preselected benzaldehyde with a preselected p-amino benzene alkanoic or alkenoic acid. The resulting Schiff base is reduced to prepare the corresponding free acid. A convenient method of carrying out the later procedure involves mixing about 0.1 mol. of the Schiff base with an excess of ethanol and water. Dilute aqueous sodium hydroxide in an amount of about 1.0 molar equivalent of the Schiff base optionally can be added to the mixture. Sodium borohydride or other suitable reducing agent (0.1 mol.) is added at about room temperature and stirred until it dissolves. The mixture is heated at reflux for about 1 or 2 hours. The product may be separated from the mixture by known procedures and further purified if desired.

Pharmaceutically-acceptable salts of the acid may be prepared by treating the free acid with an appropriate base, that is a base which will form a pharmaceutically-acceptable salt with the carboxylic acid and the anions of which are relatively innocuous at dosages consistent with good pharmacological activity so that the desired hypolipidemic properties of the salt are not vitiated by side effects ascribable to the anions.

In carrying out the method of the present invention, the active compound can be administered directly or as an active ingredient of a pharmaceutical preparation or composition. To illustrate, for oral administration, pharmaceutical preparations of the benzylaminobenzene alkanoic or alkenoic acids may be made by following the conventional techniques of the pharmaceutical chemist. These techniques involve granulating and compressing the active compound alone or in admixture with other materials or variously mixing and dissolving or suspending the active compound with other ingredients as appropriate to prepare a predetermined end product. Numerous pharmaceutical forms to carry the compound can be used. For example, the pure compound can be mixed with a solid carrier. Generally, inorganic pharmaceutical carriers are preferable and particularly solid inorganic carriers. One reason for this is the large number of inorganic materials which are known to be pharmaceutically safe and acceptable, as well as very convenient in preparing formulations. The compositions may take the form of tablets, linquets, powders, capsules, troches or lozenges and such compositions may be prepared by standard pharmaceutical techniques. Tablet compositions may be coated or uncoated and they may be effervescent or non-effervescent. Conventional excipients for tablet formations may be used. For example, inert diluents, such as magnesium carbonate, disintegrating agents such as maize starch or alginic acid, and lubricating agents such as magnesium stearate may be used.

If a liquid carrier is used, the preparation may be in the form of a soft gelatin capsule, a syrup, a liquid solution or a suspension.

The hydrocarbon solubility of the compounds of this invention generally is sufficiently high to allow the use of pharmaceutically-acceptable oils either as a solvent or as a carrier. For example vegetable or animal oils such as sunflower oil, safflower oil, mazie oil or cod liver oil can be used. Glycerine can also be used. With this latter solvent, for 2 to 30 percent water may be added. When water alone is the carrier, or when the solubility of the compound in the oil is low, the preparations can be administered in the form of a slurry.

Emulsion compositions may be formulated using emulsifying agents such as sorbitan trioleate, polyoxyethylene sorbitan monooleate, lecithin, gum acacia or gum tragacanth. Aqueous based suspensions may be prepared with the aid of wetting agents such as polyethylene oxide condensation products of alkyphenols, fatty alcohols or fatty acids with the suspending agents, for example a hydrophilic colloid such as polyvinylpyrrolidone. The emulsions and suspensions may contain conventional excipients such as sweetening agents, flowing agents, coloring materials and preservatives.

The benzylaminobenzene alkanoic or alkenoic acids, ester or salt used in the method of the present invention also can be incorporated in a nutritive foodstuff such as, for example, margarine, edible oils, casein, carbohydrates and the like. Such nutritive compositions are adapted to be administered as a partial or total diet or as a supplement to the diet. Such compositions preferably contain from about 0.02 or less to about 2 or more percent of the active ingredient when administered as the total diet. The compositions can contain higher concentrations of the active ingredient when administered as a supplement.

For parenteral use, the compounds of this invention can be formulated with sterile ingredients, compounded and packaged asceptically. They may be administered intravenously or intramuscularly. Useful solvents for formulation in such use are the polyhydric aliphatic alcohols and mixtures thereof. Especially satisfactory are the pharmaceutically-acceptable glycols, such as propylene glycol, and mixtures thereof. Glycerine is another example of a polyol which is particularly useful. Up to 25–30 percent by volume of water may be incorporated in the vehicle if desired. An 80 percent aqueous propylene glycol solution is a particularly convenient solvent system. A pH range, about 7.4, and isotonicity compatible with body isotonicity, is desirable. Basicity may be controlled by addition of a base is required, and a particularly convenient base is monoethanolamine. It may often be desirable to incorporate a local anesthetic and such are well known to those skilled in the art.

The percentage of the compound to be used in the pharmaceutical carrier may be varied. It is necessary that the compound constitute a proportion such that a suitable dosage will be obtained and it is preferred to use pharmaceutical compositions containing at least 10 weight percent of the compound. Activity increases with concentration of the agent in the carrier, but those compositions containing a significant amount of carrier, e.g. at least 1 percent and preferably at least 5 percent, are preferred as they allow for the easier administration of the compound.

The following examples will serve to further clarify the invention, but are not to be construed as a limitation thereon.

EXAMPLE 1

Preparation of 4-(((4-Fluorophenyl)methyl)amino)benzenepropanoic Acid

A mixture of p-fluorobenzaldehyde (3.83 g, 0.031 mol) and 5.1 g (0.031 mol) of 3-(4-amino)benzenepropanoic acid with a trace of p-toluene sulfonic acid in 100 ml of toluene was refluxed for about one hour. Water was collected in a Dean-Stark trap. At the end of this period the solvent was evaporated under reduced pressure and the pale yellow residue was redissolved in 100 ml of ethanol. Powdered sodium borohydride (1.2 g, 0.031 mol) was added carefully with enough water to give a clear solution. The resulting mixture was refluxed for about one additional hour.

Part of the ethanol was evaporated and the remaining reaction mixture was poured into about one liter of ice water and neutralized with dilute hydrochloric acid. The crude title compound precipitated as a white solid which was collected on a filter, washed with water, and dried in air. The crude product was recrystallized from 30 ml of toluene to give 3.96 grams (47% yield) of the crystalline title compound. The melting point was found to be 147°–148.5° C.

Elemental analysis found carbon 70.17%, hydrogen 5.98%, and nitroogen 4.98% as compared to calculated values of carbon 70.31%, hydrogen 5.90%, and nitrogen 5.13%.

Other compounds corresponding to the general formula

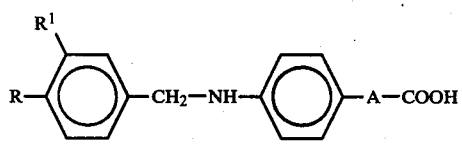

were also prepared using the method of synthesis described above. The compounds are listed in Table 1 below.

TABLE 1

| Compound Example No. | R | R' | A | Melting Point Degrees C. |
| --- | --- | --- | --- | --- |
| 2 | H | —OCH₃ | —C₂H₄— | 89–90 |
| 3 | —CH₃ | H | —C₂H₄— | 125–127 |
| 4 | H | H | —C₂H₄— | 108–110 |
| 5 | Cl | H | —C₂H₄— | 135–136 |
| 6 | Cl | Cl | —C₂H₄— | 81–82 |
| 7 | —O—CH₂—O— | | —C₂H₄— | 120–121 |
| 8 | H | H | —C₃H₆— | 64–65 |
| 9 | F | H | —C₃H₆— | 73–74 |
| 10 | Cl | Cl | —C₃H₆— | 91–94 |
| 11 | H | H | —CH=CH— | 172–173 |
| 12 | Cl | Cl | —CH=CH— | 205 |

The hypolipidemic effect of the compounds of the invention was illustratively demonstrated in rats. In this procedure an active compound as herein disclosed was dissolved in acetone, taken up on a silica gel and mixed with normal ground feed to yield concentrations of 0.125 percent of the compound in the animal feed. The treated feed was administered to male rats weighing 150–160 grams over a fourteen day period. Following the fourteen day feeding period, the rats were sacrificed, and the blood samples were collected. The liver was removed, weighed, and frozen for future analysis. The simultaneous determination of cholesterol and triglycerides in the serum and liver was carried out using a Technicon Auto Analyzer II ®. Using the average levels of the control rats as a standard, the mean results obtained in the treated groups was thereby ascertained.

Table 2 compares the percent change of lipid levels in the treated rats as compared to the controls.

TABLE 2

| Compound Example No. | S.C.* | S.T.* | B.W.* | L.W.* |
| --- | --- | --- | --- | --- |
| 1 | −39 | −63 | 0 | +4 |
| 2 | −6 | −60 | 0 | +13 |
| 3 | −9 | −59 | +2 | +7 |
| 4 | −28 | −73 | +1 | +6 |
| 5 | −16 | −56 | +1 | +7 |
| 6 | −29 | −59 | 0 | +3 |
| 7 | −39 | −50 | +4 | +22 |
| 8 | −16 | −82 | 0 | +27 |
| 9 | −6 | −85 | −3 | +25 |
| 10 | −31 | −70 | +2 | +41 |
| 11 | −14 | −29 | −2 | −8 |

TABLE 2-continued

| Compound Example No. | S.C.* | S.T.* | B.W.* | L.W.* |
| --- | --- | --- | --- | --- |
| 12 | −30 | −39 | 0 | 0 |

*all data represents percent change as compared to the control group.
S.C. = serum cholesterol
S.T. = serum triglycerides
B.W. = body weight
L.W. = liver weight The data indicates that the compounds disclosed herein are effective hypocholesterolemic and hypotriglyceridemic agents. Compounds showing hypocholesterolemic activity greater than about 25% are preferred. In addition, those compounds showing minimal changes in body weight and liver weight are particularly preferred. Therefore the preferred compounds for use with the present invention are 4-(((4-fluorophenyl)methyl)amino)benzenepropanoic acid (Example 1); 4-(benzylamino)benzenepropanoic acid (Example 4); 4-(((3,4-dichlorophenyl)methyl)amino)benzene propanoic acid (Example 6); and 4-(((3,4-dichlorophenyl)methyl)amino)benzene-2-propenoic acid (Example 12).

We claim:

1. A method for lowering serum lipids in a mammal which comprises administering an effective hypolipidemic amount of a compound of the formula

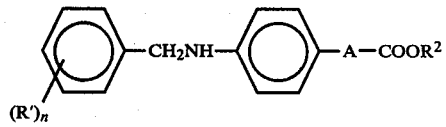

wherein R' independently and at each occurrence represents halogen, lower alkyl, lower alkoxy, or together where n=2 methylenedioxol;
R² is hydrogen or lower alkyl;
n is the integer 0, 1, 2 or 3; and
A is ethylidene or a saturated hydrocarbon of the general formula —(CH₂)ₘ— wherein m is an integer of from 2 to about 3 with the proviso that when m is 3, R' is not methylenedioxol and further including the pharmaceutically-acceptable salts of the acid.

2. The method of claim 1 wherein A is a saturated hydrocarbon containing three carbon atoms.

3. The method of claim 2 wherein A is ethylidene.

4. The method of claim 2 wherein the compound is 4-(((4-fluorophenyl)methyl)amino)benzene propanoic acid or a pharmaceutically-acceptable salt thereof.

5. The method of claim 2 wherein the compound is 4-(((3,4-dichlorophenyl)methyl)amino)benzene propanoic acid or a pharmaceutically-acceptable salt thereof.

6. The method of claim 2 wherein the compound is 4-(benzylamino)benzene propanoic acid or a pharmaceutically-acceptable salt thereof.

7. The method of claim 3 wherein the compound is 4-(((3,4-dichlorophenyl)methyl)amino)benzene-2-propenoic acid or a pharmaceutically-acceptable salt thereof.

* * * * *